United States Patent
Wu et al.

(10) Patent No.: US 9,441,015 B2
(45) Date of Patent: Sep. 13, 2016

(54) RECOMBINANT FUSION ANTIGEN GENE, RECOMBINANT FUSION ANTIGEN PROTEIN AND SUBUNIT VACCINE COMPOSITION HAVING THE SAME AGAINST INFECTION OF PORCINE REPRODUCTIVE AND RESPIRATORY SYNDROME VIRUS

(71) Applicant: NATIONAL PINGTUNG UNIVERSITY OF SCIENCE AND TECHNOLOGY, Pingtung (TW)

(72) Inventors: Mei-Li Wu, Pingtung County (TW); Hso-Chi Chaung, Pingtung County (TW); Guan-Ming Ke, Pingtung County (TW)

(73) Assignee: NATIONAL PINGTUNG UNIVERSITY OF SCIENCE AND TECHNOLOGY, Pingtung (TW)

( * ) Notice: Subject to any disclaimer, the term of this patent is extended or adjusted under 35 U.S.C. 154(b) by 0 days.

(21) Appl. No.: 14/667,697

(22) Filed: Mar. 25, 2015

(65) Prior Publication Data

US 2016/0137699 A1    May 19, 2016

(30) Foreign Application Priority Data

Nov. 19, 2014    (TW) .............................. 103140120 A

(51) Int. Cl.
| | |
|---|---|
| C07K 14/005 | (2006.01) |
| C12N 7/00 | (2006.01) |
| A61K 39/39 | (2006.01) |
| A61K 39/12 | (2006.01) |
| A61K 39/00 | (2006.01) |

(52) U.S. Cl.
CPC ............. *C07K 14/005* (2013.01); *A61K 39/12* (2013.01); *A61K 2039/55561* (2013.01); *A61K 2039/70* (2013.01); *C07K 2319/00* (2013.01); *C12N 2770/10022* (2013.01); *C12N 2770/10034* (2013.01); *C12N 2770/10071* (2013.01); *C12N 2799/026* (2013.01)

(58) Field of Classification Search
None
See application file for complete search history.

(56) References Cited

U.S. PATENT DOCUMENTS

| | | | | |
|---|---|---|---|---|
| 7,608,272 | B2 * | 10/2009 | Ansari | A61K 39/12 424/204.1 |
| 2002/0172690 | A1 | 11/2002 | Calvert et al. | |
| 2010/0003288 | A1 * | 1/2010 | Chaung | A61K 39/107 424/278.1 |
| 2012/0070493 | A1 * | 3/2012 | Fraser | C07K 14/70539 424/451 |

FOREIGN PATENT DOCUMENTS

TW            201208697 A1    3/2012

OTHER PUBLICATIONS

Chia et al. (Veterinary Microbiology. 2010; 146: 189-199).*
Wang et al. (Vaccine. 2007; 25: 8220-8227).*
Fang et al. (Virus Genes. 2006; 32: 5-11).*
Sequence alignment of SEQ ID No. 2 with Geneseq access No. AZU51001 by Chuang et al in USPg Pub 20100003288.*
Bastos RG et al. "Immune response of pigs inoculated with *Mycobacterium bovis* BCG expressing a truncated form of GP5 and M protein of porcine reproductive and respiratory syndrome virus." Vaccine. Jan. 2, 2004 ;22(3-4):467-474.
Elodie Rogues et al. "Immunogenic and protective properties of GP5 and M structural proteins of porcine reproductive and respiratory syndrome virus expressed from replicating but nondisseminating adenovectors." Veterinary Research Dec. 2013, 44:17.
F. Wu et al., "Immune response to Fc tagged GP5 glycoproteins of porcine reproductive and respiratory syndrome virus.", Viral Immunol. , Sep. 2014(Epub: Jul. 11, 2014), vol. 27, No. 7, p. 343-349.

* cited by examiner

*Primary Examiner* — Shanon A Foley
(74) *Attorney, Agent, or Firm* — CKC & Partners Co., Ltd.

(57) ABSTRACT

The present invention is directed to a recombinant fusion antigen gene, a recombinant fusion antigen protein and a subunit vaccine composition having the same against infection of porcine reproductive and respiratory syndrome virus (PRRSV). A recombinant fusion antigen gene, which encodes glycoprotein GP5 with truncated N'-terminal decoy epitope, a linker sequence and membrane protein M, followed by codon optimization, is expressed by a baculovirus expression system in vitro, thereby enhancing a yield of the recombinant fusion antigen protein. The recombinant fusion antigen protein can be applied in a subunit vaccine composition, for providing vaccinated animals with better protection ability without the risks of virulent spread and virulent recovery.

6 Claims, 4 Drawing Sheets

RECOMBINANT FUSION ANTIGEN GENE, RECOMBINANT FUSION ANTIGEN PROTEIN AND SUBUNIT VACCINE COMPOSITION HAVING THE SAME AGAINST INFECTION OF PORCINE REPRODUCTIVE AND RESPIRATORY SYNDROME VIRUS

RELATED APPLICATIONS

This application claims priority to Taiwan Application Serial Number 103140120, filed Nov. 19, 2014, which is herein incorporated by reference.

BACKGROUND

1. Field of Invention

The present invention relates to a recombinant fusion antigen gene, a recombinant fusion antigen protein and a subunit vaccine composition having the same for animal use. More particularly, the present invention relates to a recombinant fusion antigen gene, a recombinant fusion antigen protein and a subunit vaccine composition having the same against infection of porcine reproductive and respiratory syndrome virus.

2. Description of Related Art

Porcine reproductive and respiratory syndrome (PRRS) was first reported in the Northern America in 1987. Several years later, PRRS and results in global outbreaks successively and great economic losses of the swine industry. As for the global swine industry, the urgent problem to be solved is how to prevent and control PRRS. PRRS probably occurs in all ages of pigs, resulting in physiological disorders, respiratory tract syndrome and death. PRRS is caused by porcine reproductive and respiratory syndrome virus (PRRSV). PRRSV belongs to the Arteriviridae family, including a positive-sense, single stranded RNA genome with viral envelope, and the diameter of the virus particle is 50-70 nm. The PRRSV genome is approximately 15 kb in the full length and encodes 10 open reading frames (ORFs). 26 kDa of glycoprotein 5 (GP5) is encoded by ORF5 and 19 kDa of unglycosylated membrane protein (M) is encoded by ORF6.

There are three major types of commercial PRRS vaccines, including live attenuated vaccines, killed vaccines and subunit vaccines produced by *Escherichia coli* (*E. coli*). The live attenuated vaccines can stimulate cellular and humeral immune responses, but the titer of the neutralizing antibody is less, resulting in insufficient protection ability and the risks of virulent spread and virulent recovery. The killed vaccines have no the risks of virulent spread and virulent recovery; however, the killed vaccines merely evoke the humeral immune response and they cannot provide protection ability against heterologous virus infection, so that it is necessary to immunizing the killed vaccines twice for providing a sufficient protection ability. In addition, there is no exact data to show that the subunit vaccines produced by *E. coli* can provide sufficient protection ability.

The PRRSV evolves and mutates extremely fast due to RNA virus. There is, however, a growing need for new vaccines with safety and protection ability without no risks of virulent spread and virulent recovery is emerging, for overcoming all issues of conventional vaccines.

SUMMARY

Accordingly, the invention provides an isolated nucleic acid comprising a recombinant fusion antigen gene of SEQ ID NO.: 1 encoding a recombinant fusion antigen protein. The recombinant fusion antigen gene combines a nucleic acid sequence encoding glycoprotein GP5 of porcine reproductive and respiratory syndrome virus (PRRSV) with truncated N'-terminal decoy epitope, a linker sequence and membrane protein M, followed by codon optimization.

Moreover, the present invention provides a recombinant viral vector comprising a recombinant fusion antigen gene of SEQ ID NO.: 1 encoding a recombinant fusion antigen protein.

Furthermore, the present invention provides a recombinant fusion antigen protein comprising a recombinant protein expressed by a nucleic acid sequence of SEQ ID NO.: 1 in a recombinant baculovirus expression system, thereby increasing an expression yield of the recombinant fusion antigen protein.

Still further, the present invention provides a subunit vaccine composition of anti-porcine reproductive and respiratory syndrome virus (PRRSV) infection comprising a recombinant fusion antigen protein and a pharmaceutically acceptable carrier, in which the recombinant fusion antigen protein is expressed by a nucleic acid sequence of SEQ ID NO.: 1 in a recombinant baculovirus expression system, so as to provide vaccinated animals with better protection ability without the risks of virulent spread and virulent recovery.

According to the aforementioned aspect, the invention provides an isolated nucleic acid comprising a recombinant fusion antigen gene of SEQ ID NO.: 1 encoding a recombinant fusion antigen protein.

According to the aforementioned aspect, the present invention further provides a recombinant viral vector comprising a recombinant fusion antigen gene of SEQ ID NO.: 1 encoding a recombinant fusion antigen protein.

According to the aforementioned aspect, the present invention further provides a recombinant fusion antigen protein comprising a recombinant protein expressed by a nucleic acid sequence of SEQ ID NO.: 1 in a recombinant baculovirus expression system.

According to the aforementioned aspect, the present invention further provides a subunit vaccine composition of anti-porcine reproductive and respiratory syndrome virus (PRRSV) infection comprising a recombinant fusion antigen protein and a pharmaceutically acceptable carrier.

According to an embodiment, the aforementioned pharmaceutically acceptable carrier comprises an adjuvant and/or an immunopotentiator. In an example, the immunopotentiator includes a CpG potentiator having a nucleic acid sequence of SEQ ID NO.: 2.

With application to the recombinant fusion antigen gene, the recombinant fusion antigen protein and the subunit vaccine composition having the same against infection of PRRSV of the present invention, the recombinant fusion antigen gene that combines the nucleic acid sequences of the glycoprotein GP5 with truncated N'-terminal decoy epitope, the linker sequence and the membrane protein M, followed by codon optimization, is expressed by a baculovirus expression system in vitro, thereby enhancing the yield of the recombinant fusion antigen protein. The recombinant fusion antigen protein can provide vaccinated animals with better protection ability without the risks of virulent spread and virulent recovery when being applied in a subunit vaccine composition. Therefore, the problems such as less yield of PRRSV antigen, worse protection ability, the risks of virulent spread and virulent recovery existed in conventional PRRSV vaccines can be effectively improved.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1A:
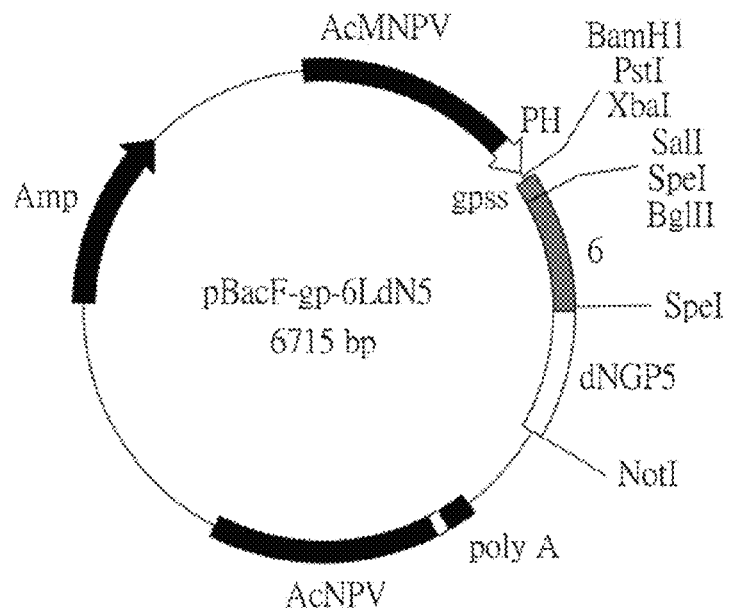
FIG. 1A is a map of a recombinant viral vector according to one embodiment of the present invention.

Reference will now be made in detail to the present embodiments of the invention, examples of which are illustrated in the accompanying drawings. Wherever possible, the same reference numbers are used in the drawings and the description to refer to the same or like parts.

As aforementioned, the present invention relates to a recombinant fusion antigen gene and a recombinant fusion antigen protein expressed by the same against infection of porcine reproductive and respiratory syndrome virus (PRRSV). The recombinant fusion antigen gene combines a nucleic acid sequence encoding a glycoprotein GP5 with truncated N'-terminal decoy epitope, a linker sequence and a membrane protein M, followed by codon optimization, is expressed by a baculovirus expression system in vitro, thereby enhancing a yield of the recombinant fusion antigen protein.

Typically, the "recombinant fusion antigen gene" as discussed hereinafter denotes a nucleic acid sequence of SEQ ID NO.: 1. In an embodiment, the recombinant fusion antigen gene combines a nucleic acid sequence encoding glycoprotein GP5 of PRRSV with truncated N'-terminal decoy epitope, a linker sequence and membrane protein M gene.

More specifically, two major envelope proteins of the viral envelop of PRRSV, the glycoprotein GP5 and the membrane protein M, associate into a disulfide-linked heterodimer, which together encompass at least half of the total viral protein. The glycoprotein GP5 and the membrane protein M both induce protective immune response and neutralizing antibodies of the host. However, the N'-terminal decoy epitope of the glycoprotein GP5, approximately 30 amino acids, eliminates the production and the reactivity of the neutralizing antibodies. Therefore, one of the features of the present invention is to provide a truncated N'-terminal decoy epitope of the glycoprotein GP5, in which the first to the tenth amino acid of N'-terminal decoy epitope is deleted, and the nucleic acid sequence encoding glycoprotein GP5 with truncated N'-terminal decoy epitope is connected to the nucleic acid sequence encoding the membrane protein M via the linker sequence, and the whole nucleic acid sequence is subjected to codon optimization. Such recombinant fusion antigen gene can increase the yield of the recombinant fusion antigen protein in the baculovirus expression system, and the resultant recombinant fusion antigen protein has accurate tertiary structure and folding after being post-translationally modified by the eukaryotic expression system.

The "linker sequence" as discussed hereinafter denotes a nucleic acid sequence for connecting the nucleic acid sequence of the glycoprotein GP5 and the nucleic acid sequence of the membrane protein M. There is no limitation to the length of "linker sequence", for example, 6 nucleotides to 30 nucleotides, preferably 9 nucleotides to 24 nucleotides, and more preferably 9 nucleotides to 15 nucleotides. In an example, the "linker sequence" has 12 nucleotides.

The "codon optimization" as discussed hereinafter denotes to select codons based on the preferred codons of the baculovirus expression system without changing the original amino acid sequence, so as to provide immune protection effect. The reason is that *E. coli* cannot provide accurate post-translational modification such as glycosylation although *E. coli* is the very popular protein expression system because of its advantages such as fast growth rate, high yield and low cost. The *E. coli* expression system will probably produce insoluble inclusion of the recombinant protein. In comparison, the baculovirus expression system can produce the recombinant protein in mass and accurate post-translational modification such as glycosylation. In an embodiment, the resultant recombinant fusion antigen protein has accurate sugar residues and folding structure.

The aforementioned sequence of the recombinant fusion antigen gene (or called as 6LdN5) is compared to the original (or called as wild-type) gene sequence using commercial sequencing analysis programs (for example, DNAStar software) and the result is listed in TABLE 1.

TABLE 1

| Percentage of Identity | | | | |
| --- | --- | --- | --- | --- |
| Divergence | 1 | 2 | | |
| 1 |  | 89.5 | 1 | 6LdN5 |
| 2 | 11.4 |  | 2 | wild-type |
|  | 1 | 2 | | |

As the comparison result shown in TABLE 1, the recombinant fusion antigen gene (or called as 6LdN5) is subjected to codon optimization and has a percentage identity of 89.5% with the original (or called as wild-type) gene sequence.

The "recombinant baculovirus expression system" as discussed hereinafter is referred to a gene expression system consisting of baculovirus expression vector (BEV) and its host insect cell. The baculovirus is a large DNA virus that infects invertebrates, primarily insects and some arthropods. The baculovirus expression vector system (BEVS) developed from baculovirus provides relative safety because human and other vertebrates are not the hosts of baculoviruses. The aforementioned BEV is referred to a recombinant baculovirus carrying an exogenous gene. Once the BEV infects a host insect cell, the strong promoter of the BEV control the expression of the exogenous gene, for producing the recombinant protein in mass. The post-translational modifications of the recombinant protein obtained by the BEVS are similar to the ones obtained by the mammalian cell, so that the antigenicity, immunogenicity and bioactivities of the recombinant protein produced by the BEVS are very similar and substantially identical to the original protein.

In an example, when the recombinant fusion antigen gene is constructed into the BEV, the 5' end of the recombinant fusion antigen gene is optionally linked to the signal peptide gene sequence of the membrane glycoprotein gp64 of the baculovirus. The gp64 signal peptide residue is probably cleaved from the recombinant fusion antigen protein during the whole recombinant fusion antigen protein is transported in the cell.

In application, the recombinant fusion antigen protein and a pharmaceutically acceptable carrier can be utilized to produce a subunit vaccine composition for immunizing the pigs. In an embodiment, the pharmaceutically acceptable carrier includes an adjuvant and/or an immunopotentiator. There is no specific limitation on kinds of the adjuvants, examples of which can include but be not limited to aluminum gel adjuvant, oil adjuvant (for example, Freund's complete adjuvant, Freund's incomplete adjuvant and so on) or any combination thereof. The immunopotentiator can be exemplified as immunostimulatory oligonucleotides containing CpG motif (or called as CpG potentiator). In an example, the CpG potentiator can be a nucleic acid sequence of SEQ ID NO.: 2, for example. In an embodiment, the aforementioned subunit vaccine composition containing the CpG potentiator can immunize pigs for providing 100% of protection against PRRSV infection The recombinant fusion antigen protein of the present invention is to combine a nucleic acid sequence encoding glycoprotein GP5 of PRRSV having truncated N'-terminal decoy epitope with the membrane protein M gene, both of which a linker sequence is interposed between, and then the whole nucleic acid sequence is subjected to codon optimization, for increasing the yield of the recombinant protein expressed in the insect cell. Moreover, the recombinant viral vector carrying the recombinant fusion antigen gene transfects the recombinant baculovirus expression system for effectively increasing the yield of the recombinant fusion antigen protein.

Furthermore, the present invention adopts the recombinant baculovirus expression system for producing the recombinant fusion antigen protein in a suspension culture, which has advantages of easy manipulation, high yield, easy to enlarging the production scale. The resultant antigen protein can be produced and possess the original biological functions because the host insect cell is able to perform accurate post-translational modifications that are very similar to mammalian cells. Evidenced by the following animal immune experiments, the subunit vaccine composition including the recombinant fusion antigen protein can provide vaccinated animals with 100% of protection ability without the risks of virulent spread and virulent recovery. Consequently, the technology of the present invention can be expected to suitable for new formulations of PPRSV vaccine compositions, thereby preventing and treating of the PPRS.

Thereinafter, various applications of the method of traceless labeling glycoproteins on a surface and applications thereof will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

Example 1

Establishment of Recombinant Viral Vector of pBacF-gp-6LdN5

In this embodiment, the 6LdN5 recombinant fusion antigen gene was designed according to Genbank sequence accession number AF035409 that includes PRRSV ORF5 (the glycoprotein GP5) and ORF6 (the membrane protein M) published in the National Center for Biotechnology Information (NCBI).

Reference was made to the nucleic acid sequence of SEQ ID No.: 1. At first, a ORF6 (the $145^{th}$ nucleotide to the $681^{th}$ nucleotide) was designed before a ORF5 (the $694^{th}$ nucleotide to the $1266^{th}$ nucleotide), and a linker sequence (the $682^{th}$ nucleotide to the $693^{th}$ nucleotide) was interposed between the ORF6 and the ORF5. There were some recognition sites of restriction enzymes, Sal I (the $121^{th}$ nucleotide to the $126^{th}$ nucleotide), multiple-restriction enzyme site sequence (the $127^{th}$ nucleotide to $144^{th}$ nucleotide) and Not I (the $1288^{th}$ nucleotide to $1295^{th}$ nucleotide), are designed at two ends of fragments of the ORF5 and the ORF 6 respectively. The 5' end of the Sal I recognition site was further linked to the gp64 signal peptide gene sequence (the first nucleotide to the $120^{th}$ nucleotide) of the pBacF-gp transfer vector, for linking the N' end sequence of the PRRSV ORF6 to the gp64 signal peptide. The downstream of the ORF5 (the 694 nucleotide to the $1266^{th}$ nucleotide) was further linked to His tag (the $1267^{th}$ nucleotide to the $1284^{th}$ nucleotide) and stop codon (the $1285^{th}$ nucleotide to the $1287^{th}$ nucleotide). The whole sequence was subjected to codon optimization using commercially available softwares, for example, Codon Optimization Services provided by Genomics BioSci & Tech, Ltd. or others such as Codon Optimization Calculator provided by EnCor Biotechnology Inc., GeneGPS® Expression Optimization Technology provided by DNA2.0, Inc., Codon Optimization and Verification Services provided by ProteinCT Biotech or the like, so as to synthesize the recombinant gene called 6LdN5 in the size of 1295 bp.

The nucleic acid fragment of the recombinant fusion antigen gene 6LdN5 was purified and ligated to the pBacPAK8-gp transfer vector (i.e. the baculovirus viral vector, which had a nucleic acid sequence of the gp64 signal peptide), so as to construct the recombinant viral vector.

The pBacPAK8-gp transfer vector had a full length of 5.5 kb approximately, which included a gene of *Autographa californica* multiple nuclear polyhedrosis virus (AcMNPV) and provided a sequence for recombining the insert DNA. The pBacPAK8 transfer vector further included high-level expression of polyhedrin promoter (PPH), ampicillin (Amp) resistance gene as a selective marker and SV40 polyadenylation signal. The recombinant fusion antigen gene 6LdN5 was ligated with the pBacPAK8-gp transfer vector (carrying the nucleic acid sequence of the gp64 signal peptide) to form the recombinant viral vector (or called pBacPAK8-gp-6LdN5) in the size of 6.5 kb, as shown in FIG. 1A.

The resulted recombinant viral vector (or called pBacPAK8-gp-6LdN5) was transformed into a competent cell of *Escherichia coli* XL-1 Blue (Invitrogen, California, USA), and antibiotic resistance was used to select a clone that was successful transformed and inserted by a target gene. Besides, the target gene was cut by the restriction enzymes Xba I (located on pBacPAK8-gp viral vector and close to an upstream of 5' end of the gp64 nucleic acid sequence) and Not I and analyzed by DNA electrophoresis, and the result was shown in FIG. 1B.

Figure 1B:
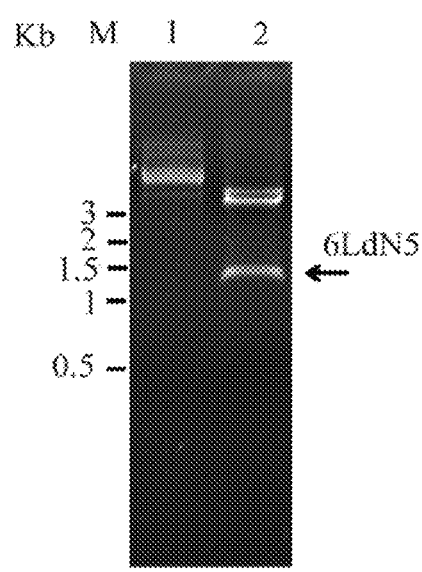
FIG. 1B is an electrophoresis image of the recombinant viral vector digested by restriction enzymes according to one embodiment of the present invention.

Reference was made to FIG. 1B, which was an electrophoresis image of the recombinant viral vector digested by restriction enzymes according to one embodiment of the present invention. In FIG. 1B, the lane M referred to DNA markers, the first lane referred to DNA fragments from the recombinant viral vector pBacPAK8-gp digested by the restriction enzymes Xba I and Not I, and the second lane referred to DNA fragments from the recombinant viral vector pBacPAK8-gp-6LdN5 digested by the restriction enzymes Xba I and Not I. The band of FIG. 1B at the 1295 bp was the DNA fragment including the recombinant gene 6LdN5 and a partial sequence of the viral vector.

Figure 2:
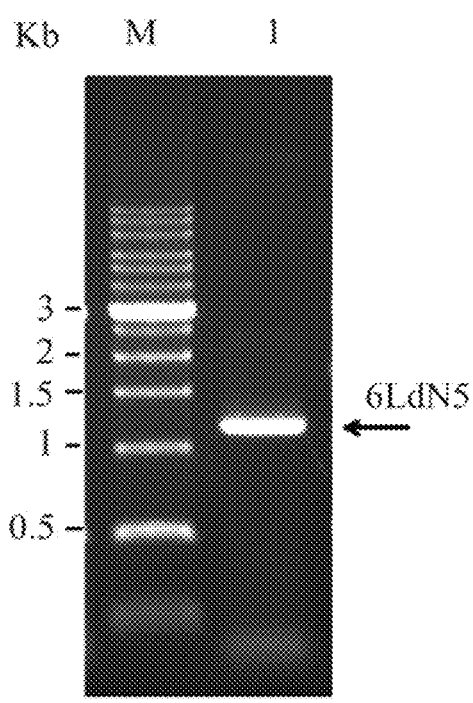
FIG. 2 is an electrophoresis image of polymerase chain reaction (PCR) product of the recombinant viral vector amplified by the PCR reaction according to one embodiment of the present invention.

In addition, the transformed clone was subjected to a polymerase chain reaction (PCR) reaction and DNA electrophoresis analysis, and the result was shown in FIG. 2. A reactant of the PCR reaction was prepared by 5 µL of 2×PCR Mastermix (0.5 U SuperTherm DNA polymerase mix, 200 µM dNTPs, 1.5 mM MgCl$_2$, 1× buffer) (Bertec, Taiwan), 1 µL of 2.5 mM 6L5(SalI) forward primer, 1 µL of 2.5 mM 5his(NotI) reverse primer and 3 µL of double-deionized water (ddH$_2$O). The reactant was reacted at 94° C. for 5 minutes, and then repeated for 30 cycles of three steps including DNA denaturation at 94° C. for 1 minute, DNA-primer annealing at 56° C. for 90 seconds and DNA extension at 72° C. for 1 minute. After the cycles were completed, the reactant was subjected to a further DNA extension at 72° C. for 7 minutes. After the whole PCR reaction was finished, 4 µL of PCR product was analyzed by 1% agarose gel electrophoresis. The sequence of the 6L5(Sa/I) forward primer was listed as SEQ ID NO: 3, and the sequence of the 5his(NotI) reverse primer was listed as SEQ ID NO: 4. The DNA sequence amplified by the pair of 6L5(SalI) and 5his(NotI) primers included the nucleic acid sequence encoding glycoprotein GP5 with truncated N'-terminal decoy epitope, the linker sequence and the membrane protein M without the nucleic acid sequence encoding the gp64 signal peptide.

Reference was made to FIG. 2, which was an electrophoresis image of PCR product of the recombinant viral vector amplified by the PCR reaction according to one embodiment of the present invention. In FIG. 2, the lane M referred to DNA markers, the first lane referred to DNA fragment of the PCR product with the size of 1151 bp amplified from the recombinant viral vector pBacPAK8-gp-6LdN5 was determined by 1% agarose gel electrophoresis.

The transformant preliminarily determined as above was further subjected to nucleic acid sequencing using an auto-sequencing apparatus such as DNA Analyzer (ABI 3730, CD Genomics, USA) of Tri-I Biotech, Inc. (Taipei, ROC) and the insert sequence was correct. The transforming vector, cell transformation, screening of the target strain, extraction of the vector DNA, the digestion of restriction enzymes, PCR reaction, DNA electrophoresis, DNA sequencing and so on should be well known by the person skilled in the art rather than reciting them in detail.

Example 2

Establishment of Recombinant Baculovirus Expression System

1. Insect Cell Culture

In the embodiment, Sf9 cell line (BCRC 60011; ATCC CRL-1711) from the fall armyworm (*Spodoptera frugiperda*) pupal ovarian tissue or High Five (abbreviated as Hi-5) cell line (BTI-TN-5B1-4)(for example, Invitrogen Co.) from pink shrimp (*Trichoplusia ni*) egg were used to establish the recombinant baculovirus expression system.

9 mL of Sf-9 or Hi-5 cell culture medium was added into 10-cm culture plates. Next, the cryovials of Sf-9 or Hi-5 cells were quickly thawed in the water bath at 37° C., and then the Sf-9 or Hi-5 cells were uniformly dispersed in the Sf-9 or Hi-5 cell culture medium respectively. Afterwards, the cell plates were cultured in the incubator at 28° C., and those cells were grown adherently and exhibited smooth and round shapes.

The Sf-9 cell culture medium was Grace's Insect cell culture medium, which contains 0.35 g $NaHCO_3$, 3 g Lactalbumin hydrolysate, 20 mL yeastolate and 10% FBS in 1000 mL of the cell culture medium, supplemented with 10,000 unit/mL of penicillin/streptomycin. The Hi-5 cell culture medium was exemplified as Sf-900II™ SFM (Invitrogen/GIBCO, USA).

2. SF-9 Cell Transfection $3\times10^5$/mL of Sf9 cells were seeded in the 12-well tissue culture plate and placed at room temperature for at least 1 hour until the cells were adhered. 1 μg of the recombinant viral vector DNA, 2 μL flashBAC DNA and 6 μL of Cellfectin® Reagent (Invitrogen®) were mixed well in unsupplemented Grace's Medium (Gibco®) and placed at room temperature for 45 minutes, for forming a mixture. Next, the cell supernatant was removed from the 12-well tissue culture plate, the cells were washed by Sf-900 II SFM in twice and the cell medium was removed. Subsequently, 1 mL of the aforementioned mixture was added to the cells in each well of the 12-well tissue culture plate, placed and cultured at 27° C. for 5 hours. After removing the supernatant, 1 mL of growth medium (TNM-FH; Sigma-Aldrich Co. LLC., USA) was added to the cells in each well of the 12-well tissue culture plate, placed and cultured at 27° C. for 5 days or until cytopathic effects were observed.

3. Isolation of Recombinant Baculovirus and Amplification of Virus Titer

When cytopathic effects (CPEs) were observed after the transfected Sf9 cells were cultured for 3 to 5 days, the recombinant baculovirus could be ready for harvest.

At first, the supernatant of the transfected Sf9 cells was transferred into 1.5 mL-microcentrifuge tubes and centrifuged at 1,000×g for 5 minutes. Afterwards, the virus stock solution including the passage zero (P0) recombinant baculovirus was aliquoted to freshly 1.5 mL-microcentrifuge tubes with dark brown color, and stored at −80° C. for preventing from light.

$3\times10^5$ cells/mL of Sf9 cells were uniformly reseeded into the 12-well tissue culture plate and placed at room temperature for at least 1 hour until the cells were adhered. 15 μL of the P0 virus stock solution was added to the cells in each well of the 12-well tissue culture plate, placed and cultured at 27° C. for 5 days, thereby harvesting the P1 recombinant virus. During harvesting the P1 virus, the supernatant of the transfected Sf9 cells was transferred into 1.5 mL-microcentrifuge tubes and centrifuged at 1,000×g for 5 minutes. Afterwards, the virus stock solution including the P1 recombinant baculovirus was aliquoted to freshly 1.5 mL-microcentrifuge tubes with dark brown color, and stored at −80° C. for preventing from light.

The aforementioned steps were repeated for amplifying the yield of the P2 recombinant baculovirus. The virus stock solution including the P2 recombinant baculovirus was stored at −80° C.

Example 3

Evaluation of Expression of Recombinant Fusion Antigen Protein Using Recombinant Baculovirus Expression System

1. Isolation of Recombinant Fusion Antigen Protein 25 mL of 1×10$^6$ cells/mL of Hi-5 cell was seeded into a 125 mL culture flask, added with the recombinant baculovirus and cultured at 27° C. for 3 to 5 days. And then, the cells were harvested and the supernatant was removed by centrifugation at 4° C. and 10,000×g for 10 minutes. The cell pellet was broken by ultrasonic vibration, and the recombinant fusion antigen protein (or called BV-gp6LdN5) was isolated and quantified, which was further analyzed by SDS-polyacrylamide gel electrophoresis (SDS-PAGE) and Western blotting.

2. Evaluation of SDS-PAGE

The well-quantified sample protein was mixed well in the 4× Sample Buffer, boiled in the boiling water for 5 minutes, denatured by SDS and carried uniformly with negative charges. Glass plates were set up, pure water was fulfilled and all equipments were tested well. All reagents listed in TABLE 2 were added sequentially, so as to make the separating gel.

TABLE 2

| Reagents | Volume |
| --- | --- |
| 10% APS | 50.00 μL |
| 10% SDS | 50.00 μL |
| 1.5M Tris-HCl (pH 8.8) | 1.25 mL |
| 40% Acrylamide/Bisacrylamide | 1.25 mL |
| TEMED | 4.00 μL |
| ddH$_2$O | 2.40 mL |
| Total | 5.00 mL |

The separating gel solution was prepared well and poured slowly into the space between the two parallel glass plates, and a little ddH$_2$O slightly covered the upper interface of the separating gel. After 25 minutes, the separating gel was gelled and polymerized, and the filter paper was used to soak up the remaining ddH$_2$O on the upper interface of the separating gel. Following, all reagents listed in TABLE 3 were added sequentially, so as to make the stacking gel.

TABLE 3

| Reagents | Volume |
| --- | --- |
| 10% APS | 25.00 μL |
| 10% SDS | 25.00 μL |
| 1.5M Tris-HCl (pH 6.8) | 0.32 mL |
| 40% Acrylamide/Bisacrylamide | 0.31 mL |
| TEMED | 2.50 μL |
| ddH$_2$O | 1.80 μL |
| Total | 2.50 mL |

After 15 minutes, the stacking gel was gelled and polymerized, and then the samples were loaded into the stacking gel. The two glass plates were assembled on the vertical electrophoresis tank, and 1× Running buffer was added therein. The samples were loaded into the stacking gel, and the proteins of the samples were separated in the stacking gel at 60 V and in the separating gel at 120 V. After 3 hours, the electrophoresis was completed, resulting in FIG. 3.

Figure 3:
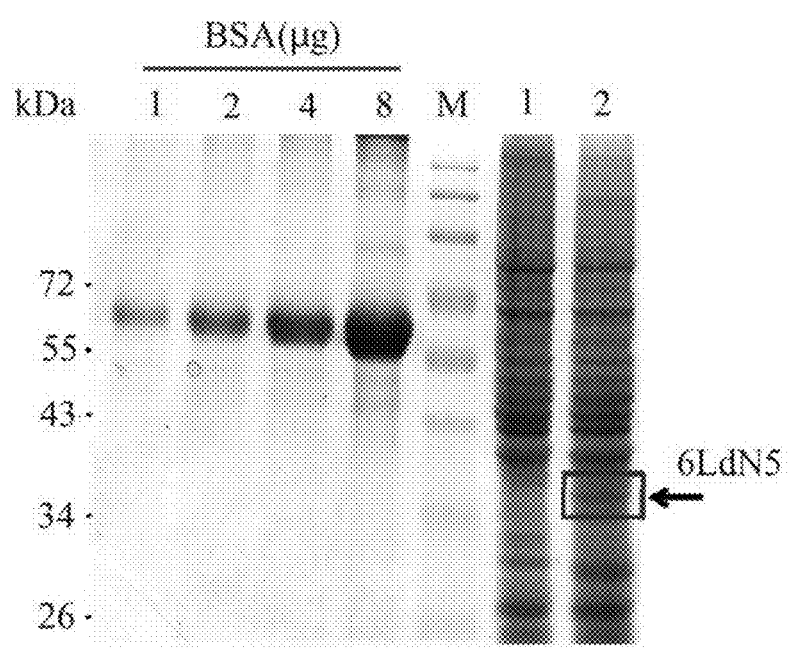
FIG. 3 is a image of SDS-polyacrylamide gel electrophoresis (SDS-PAGE) of the recombinant fusion antigen expressed by Hi-5 insect cells according to an embodiment of the present invention.

Reference was made to FIG. 3, which was an image of SDS-polyacrylamide gel electrophoresis (SDS-PAGE) of the recombinant fusion antigen expressed by Hi-5 insect cells according to an embodiment of the present invention. In FIG. 3, the bands of 1 μg, 2 μg, 4 μg, 8 μg of BSA was used to establish a standard curve, the lane M referred to protein makers, the lane 1 referred to bands of Hi-5 cellular proteins, the lane 2 referred to bands of the recombinant fusion antigen expressed by Hi-5 insect cells. As shown in the bands of FIG. 3, the recombinant fusion antigen expressed by Hi-5 insect cells had a size of 41 kDa.

3. Evaluation of Western Blotting

After the aforementioned SDS-PAGE protein electrophoresis was completed, the glass plates were disassembled and the stacking gel was removed, the separating gel was immersed in a transfer buffer for 10 minutes. Whatman 3M filter paper (Advantec, Japan) was pre-immersed in the Transfer buffer and placed on the blotting clamp. PVDF transfer membrane (Immobilon TM-P Transfer Membrane, Millipore, Ireland) with a desired size was immersed in 100% methanol for 5 minutes approximately, immersed in the transfer buffer for overflowing the upper surface of the PVDF transfer membrane and then placed on the filter paper. The SDS-PAGE gel immersed in the transfer buffer was put upon the PVDF transfer membrane, a filter paper was placed on the gel, and all layers were clamped together and put into the blotter. The side of the PDVF transfer membrane faced to the positive pole, the other side of the gel faced the negative pole, and a blotting was carried out at 250 mA for 75 minutes.

The transferred PVDF membrane was washed by 1×PBST (phosphate-buffered saline with tween 20) for 5 minutes, and immersed and shaked in a Blocking buffer at 4° C. for 1 hour. Next, the PVDF membrane was incubated in a primary antibody (mouse anti-His monoclonal antibody, Rural Technologies, Inc.; diluted 1:2,000 in 1×PBST) at 4° C. for 18 hours with gentle shaking. After the primary antibody was removed, the PVDF membrane was washed by 1×PBST for several times and incubated in a secondary antibody (goat anti-mouse IgG-HRP, Chemicon, USA; diluted 1:15,000 in 1×PBST) at 4° C. for 60 minutes with gentle shaking. After the secondary antibody was removed, the PVDF membrane was washed by 1×PBST for several times. Next, the PBST was removed, and then the PVDF membrane was incubated in ECL Plus Western Blotting Detection Reagents (GE Healthcare, UK) for 1 minute. Afterwards, the PVDF membrane was put on the central platform of Chemiluminescence Camera System (SYNGENE G, J & H Technology Co., Ltd., Taiwan) and analyzed by a commercial image analysis software, so as to calculate the molecular weight of the target protein and be shown in FIG. 4.

Figure 4:
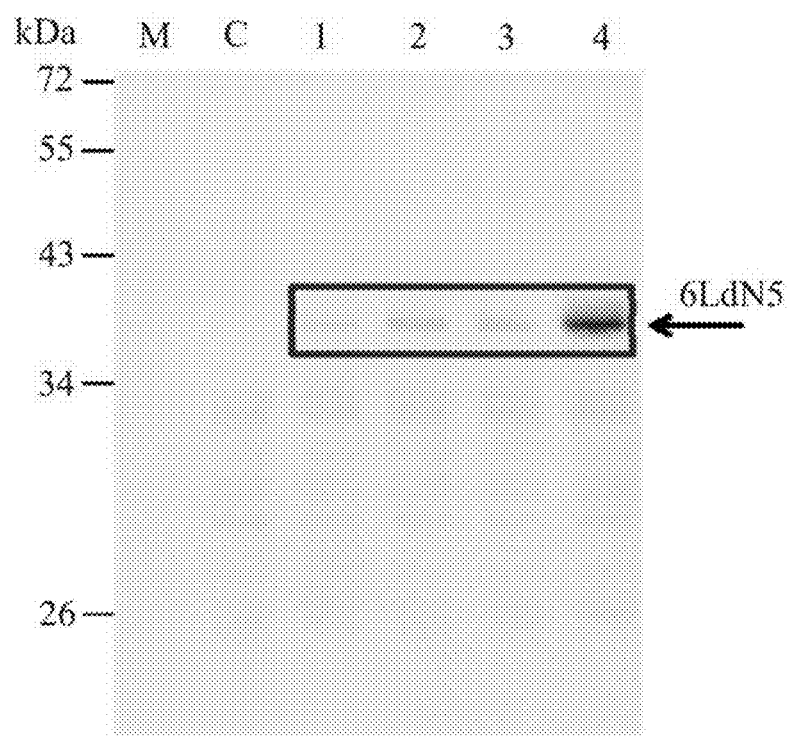
FIG. 4 is an image of Western blotting of the recombinant fusion antigen expressed by Hi-5 insect cells according to an embodiment of the present invention.

Reference was made to FIG. 4, which was an image of Western blotting of the recombinant fusion antigen expressed by Hi-5 insect cells and detected by anti-His monoclonal antibody according to an embodiment of the present invention. In FIG. 4, the lane M referred to protein makers, the lane C referred to bands of Hi-5 cellular proteins, the lane 1 referred to bands of the recombinant fusion antigen expressed by Hi-5 insect cells on the day 2, the lane 2 referred to bands of the recombinant fusion antigen expressed by Hi-5 insect cells on the day 3, the lane 3 referred to bands of the recombinant fusion antigen expressed by Hi-5 insect cells on the day 4, and the lane 4 referred to bands of the recombinant fusion antigen expressed by Hi-5 insect cells on the day 5. As shown in the bands of the lanes 1 to 4 of FIG. 4, with increase of expression days of the recombinant fusion antigen, the yield of the recombinant fusion antigen expressed by Hi-5 insect cells was also increased. On the day 5, the yield of the recombinant fusion antigen was 533 μg/mL.

4. Evaluation of Virulence

Eight 3 to 4 week-old weaned piglets with negative for PRRSV antigen, PRRSV antibody and classical swine fever (CSF) were provided. The body temperatures of all piglets were measured prior to 3 days the virus challenge, and the piglets having the normal temperature were subjected to the virus challenge. In the PRRSV challenge, the neck of each piglet was injected intramuscularly with 3 mL of PRRSV in the virus titer of $10^{5.0} TCID_{50}/mL$. The body temperature of every piglets were monitored daily for 14 days post the PRRSV challenge. After the observation period was completed, all piglets were subjected to necropsy, so that clinical signs and pathological changes were observed, and the bloods were collected to perform PCR examination.

5. Test of Immunization Against Virus Challenge

Fifteen 3 to 4 week-old weaned piglets with negative for PRRSV antigen, PRRSV antibody and classical swine fever (CSF) were randomly divided into 3 groups. The first group: the necks of five piglets were injected intramuscularly with the recombinant fusion antigen protein and commercial oil adjuvant (for example, Freund's incomplete adjuvant), for example, 2 mL of the subunit vaccine composition (including 50 μg of the recombinant fusion antigen protein and 1.2 mL of the oil adjuvant). The second group: the necks of five piglets were injected intramuscularly with the recombinant fusion antigen protein, commercial oil adjuvant (for example, Freund's incomplete adjuvant) and a CpG potentiator (such as the nucleic acid sequence of SEQ ID NO.: 2), for example, 2 mL of the subunit vaccine composition (including 50 μg of the recombinant fusion antigen protein, 1.2 mL of the oil adjuvant and 50 μg of the CpG potentiator). The residual uninoculated piglets, which belonged to a negative control group (or called the third group), were injected intramuscularly with Hi-5 cell supernatant (including Hi-5 cellular proteins) and the oil adjuvant, for example, 125 μL of cellular cell supernatant and 1.2 mL of the oil adjuvant, and raised in isolation from other piglets. The piglets of all groups were subjected to virus challenge with PRRSV virus solution on 28 days post-immunization, intramuscularly injecting the neck of each piglet with 3 mL of PRRSV in the virus titer of $10^{5.0} TCID_{50}/mL$ and monitored for 21 days. After the observation period was completed, all piglets were subjected to necropsy, so that clinical signs, pathological changes, detection results of antigen and antibody were determined.

After the test of immunization against virus challenge, the piglets of the first group displayed 75% of the protection ability, the piglets of the second group displayed 100% of the protection ability, and the piglets of the second group displayed 0% of the protection ability. The result evidenced that the resultant subunit vaccine composition provided sufficient protection ability, and the resultant subunit vaccine composition having the immunopotentiator provided better protection ability. The subunit vaccine composition of the present invention could be applied in new formulations of PRRSV subunit vaccine composition, thereby preventing and treating of the PPRS.

It is necessarily supplemented that, specific recombinant vectors, specific expression systems, specific isolation methods, specific culturing methods, specific analysis methods or specific apparatuses are exemplified for clarifying the recombinant fusion antigen gene, the recombinant fusion antigen protein and the subunit vaccine composition having the same against infection of PRRSV of the present invention. However, as is understood by a person skilled in the art, other recombinant vectors, other eukaryotic expression systems, other isolation methods, other culturing methods, other analysis methods or other apparatuses can be also adopted in the recombinant fusion antigen gene, the recombinant fusion antigen protein and the subunit vaccine composition having the same against infection of PRRSV of the present invention, rather than being limited thereto.

According to the embodiments of the present invention, the aforementioned recombinant fusion antigen gene, the recombinant fusion antigen protein and the subunit vaccine composition having the same against infection of PRRSV of the present invention advantageously combines the nucleic acid sequences of the glycoprotein GP5 with truncated N'-terminal decoy epitope, the linker sequence and the membrane protein M into the recombinant fusion antigen gene, followed by codon optimization and expression in the baculovirus expression system in vitro, thereby enhancing the yield of the recombinant fusion antigen protein. The recombinant fusion antigen protein can provide vaccinated animals with better protection ability without the risks of virulent spread and virulent recovery when being applied in the subunit vaccine composition. Therefore, the problems such as less yield of PRRSV antigen, worse protection ability, the risks of virulent spread and virulent recovery existed in conventional PRRSV vaccines can be effectively improved.

Although the present invention has been described in considerable detail with reference to certain embodiments thereof, other embodiments are possible. Therefore, the spirit and scope of the appended claims should not be limited to the description of the embodiments contained herein.

What is claimed is:

1. An isolated nucleic acid comprising a recombinant fusion antigen gene of SEQ ID NO.: 1 encoding a recombinant fusion antigen protein.

2. A recombinant viral vector comprising a recombinant fusion antigen gene of SEQ ID NO.: 1 encoding a recombinant fusion antigen protein.

3. A recombinant fusion antigen protein comprising a recombinant protein expressed by a nucleic acid sequence of SEQ ID NO.: 1 in a recombinant baculovirus expression system.

4. A subunit vaccine composition of anti-porcine reproductive and respiratory syndrome virus (PRRSV) infection comprising a recombinant fusion antigen protein and a pharmaceutically acceptable carrier, wherein the recombinant fusion antigen protein is expressed by a nucleic acid sequence of SEQ ID NO.: 1 in a recombinant baculovirus expression system.

5. The subunit vaccine composition of anti-PRRSV infection of claim 4, wherein the pharmaceutically acceptable carrier comprises an adjuvant and/or an immunopotentiator.

6. The subunit vaccine composition of anti-PRRSV infection of claim 5, wherein the immunopotentiator comprises a CpG potentiator, and the CpG potentiator is a nucleic acid sequence of SEQ ID NO.: 2.

* * * * *

SEQUENCE LISTING

```
<160> NUMBER OF SEQ ID NOS: 4

<210> SEQ ID NO 1
<211> LENGTH: 1295
<212> TYPE: DNA
<213> ORGANISM: Artificial sequence
<220> FEATURE:
<223> OTHER INFORMATION: PRRSV RECOMBINANT FUSION ANTIGEN GENE

<400> SEQUENCE: 1
atgctgctcg ttaaccagag ccaccaaggt ttcaacaagg agcacacctc caagatggtc      60
tctgctatcg tgctctacgt cttgctggct gctgctgctc actccgcctt cgctgccgac     120
```

```
gtcgacacta gtagatctgt cgacgtcgac atggggtcgt ccctagacga cttttgtcat    180
gatagcacgg ctccacaaaa ggtgatcttg gcgttttcta tcacctacac gccagtgatg    240
atatatgccc taaaagtgag tcgcggccgg ctgctagggc tcctccacct gctaattttc    300
ctgaattgtg ccttcacctt cgggtatatg acatttgtgc actttcagag tacaaatagg    360
gtcgcgctta ctatgggagc agtagttgca ctcctttggg gggtgtattc agccatagaa    420
acttggagat tcatcacctc cagatgccgt ctgtgcttgc taggccgcag gtacattctg    480 gccectgccc accacgttga gggtgccgca ggctttcatc cgattgcggc aagtgataac    540
cacgcatttg tcgtccggcg tcccggctcc actacggtta acggcacatt ggtgcccggg    600
ttgaaaagcc tcgtgttggg tggcagaaaa gctgtaaaac agggagtggt aaaccttgtc    660
aaatatgcca agacactag tggcggcggc agcatgtcgc aattgccttt tttgtggtgt    720
atcgtgccat tctgtttagt tgcgctttcc ggcgcaaacc aaaacagcag ctcttactcc    780
cagttgattt acaacttgac gctatgtgag ctgaacggca cagattggct ggccaataag    840
tttgattggg cggttgagac tttcgtcatt tttcccgtgt tgactcacat cgtctcctac    900
ggtgccctca ccaccagcca tttccttgac acagttggct tggccaccgt gtccaccgcc    960
gggtattatc atgggcggta tgttttgagc agcatttacg cagtctgtgc cctggctgcg   1020
ttagtttgct tcgtcattag gttggcgaag aactgcatgt cctggcgcta ctcgtgtacc   1080
aggtatacca actttctcct tgacactaaa ggaaaaatct atcgctggcg atcgcccgtc   1140
attatagaaa aaggggggcaa agttgaggtt ggagatcacc ttatcggcct caagagagtt   1200
gtgctagacg gttccgcggc aaccctgta accagaattc cagcggaacg atggggtcgt   1260
cccgaccatc accatcacca tcactaggcg gccgc                              1295

<210> SEQ ID NO 2
<211> LENGTH: 230
<212> TYPE: DNA
<213> ORGANISM: Artificial sequence
<220> FEATURE:
<223> OTHER INFORMATION: CpG potentiator

<400> SEQUENCE: 2
actagttcgt cgaagtcgtt ttgggggggtc tagttcgtcg aaatcgattt gggggggtcta    60 gttcgtcgaa gtcgttttgg ggggtctagt tcgtcgaaat cgatttgggg ggtctagttc   120
gtcgaagtcg ttttgggggg tctagttcgt cgaaatcgat ttgggggggtc tagttcgtcg   180 aagtcgtttt gggggtcta gttcgtcgaa atcgatttgg ggggtctaga                230

<210> SEQ ID NO 3
<211> LENGTH: 24
<212> TYPE: DNA
<213> ORGANISM: Artificial sequence
<220> FEATURE:
<223> OTHER INFORMATION: 6L5(SalI) forward primer

<400> SEQUENCE: 3
gtcgacatgg ggtcgtccct agac                                            24

<210> SEQ ID NO 4
<211> LENGTH: 32
<212> TYPE: DNA
<213> ORGANISM: Artificial sequence
<220> FEATURE:
<223> OTHER INFORMATION: 5his(NotI) reverse primer
```

```
<400> SEQUENCE: 4
gcggccgcct agtgatggtg atggtgatgg tc                                    32
```